United States Patent
Chen

(10) Patent No.: US 6,989,001 B2
(45) Date of Patent: Jan. 24, 2006

(54) BREAKABLE SYRINGE WITH A SAFETY SLEEVE

(76) Inventor: Huang-Chuan Chen, No. 5, Lane 180, Lungshan 2 St., Taya Hsiang, Taichung Hsien (TW)

( * ) Notice: Subject to any disclaimer, the term of this patent is extended or adjusted under 35 U.S.C. 154(b) by 67 days.

(21) Appl. No.: 10/856,726

(22) Filed: May 28, 2004

(65) Prior Publication Data

US 2005/0267411 A1    Dec. 1, 2005

(51) Int. Cl.
*A61M 5/00*    (2006.01)
*A61M 5/32*    (2006.01)

(52) U.S. Cl. .................. 604/110; 604/197; 604/198; 128/919

(58) Field of Classification Search ............... 604/110, 604/192, 197, 198, 263, 187; 128/919
See application file for complete search history.

(56) References Cited

U.S. PATENT DOCUMENTS

| | | | |
|---|---|---|---|
| 3,557,784 A * | 1/1971 | Shields | 604/68 |
| 4,655,751 A * | 4/1987 | Harbaugh | 604/198 |
| 4,801,295 A * | 1/1989 | Spencer | 604/198 |
| 5,057,087 A * | 10/1991 | Harmon | 604/198 |
| 5,098,402 A * | 3/1992 | Davis | 604/195 |
| 5,122,124 A * | 6/1992 | Novacek et al. | 604/195 |
| 5,328,473 A * | 7/1994 | Fayngold et al. | 604/110 |

FOREIGN PATENT DOCUMENTS

FR    WO 9523004    * 8/1995

* cited by examiner

*Primary Examiner*—Nicholas D. Lucchesi
*Assistant Examiner*—Catherine S. Williams
(74) *Attorney, Agent, or Firm*—William E. Pelton, Esq.

(57) ABSTRACT

A breakable syringe with a safety sleeve has a syringe body (10), a needle (13) with a needle base (12), a safety sleeve (20), and a breaking device. The needle (13) is attached to the syringe body (10) by inserting the needle base (12) into the syringe body (10). The safety sleeve (20) slidably sleeves the syringe body (10) and clamps the breaking device with the syringe body (10). By sliding the safety sleeve (20), the safety sleeve (20) can be selectively positioned at different locations to expose or enclose the needle (13) by the multiple engaging devices and even to urge the breaking device to break the syringe body (10). Therefore, the needle (13) of the syringe is conveniently enclosed and the syringe can be immediately broken after use.

12 Claims, 7 Drawing Sheets

BREAKABLE SYRINGE WITH A SAFETY SLEEVE

BACKGROUND OF THE INVENTION

1. Field of the Invention

The present invention relates to a syringe, and more particularly to a breakable syringe that has a safety sleeve enclosing a needle of the syringe to protect a user and operationally urging the syringe to break after use.

2. Description of Related Art

With reference to FIG. 7, a conventional syringe comprises a tube body (30) with a chamber (31), a piston shaft (35), a needle (33) and a cap (36).

The tube body (30) has two ends, an opening (not numbered) defined at one end and a needle base (32) attached at the other end. The piston shaft (35) is slidably received inside the chamber (31). The needle (33) is firmly attached to the needle base (32) and has a channel (34) axially defined through the needle (33) to communicate with the chamber (31) of the tube body (30). The cap (36) is detachably mounted on the end having the needle (33) to protect a user from accidental pricking by the needle (33).

When the syringe is to be used, the cap (36) is removed from the tube body (30) to stick the needle (33) into a dose bottle to draw medicinal liquid into the chamber (31) by pulling the piston shaft (35) away from the needle base (32). Then, the needle (33) is inserted into a patient whereafter by pushing the piston shaft (35), the medicinal liquid is injected into the patient. After injection, the syringe has to be discarded for hygiene reasons. The cap (36) has to be mounted on the tube body (30) again to avoid the dangers of staff etc being accidentally pricked by the used needle (33) especially when patient has a fluid-transmissible disease.

However, re-mounting the cap (36) is dangerous because the needle (33) has to be precisely aligned with an entrance of the cap (36). Otherwise, the user may inadvertently touch the needle (33) and get hurt when the cap (36) moves toward the needle (33).

Additionally, the syringe is still workable after use and some unscrupulous merchant may recycle the workable syringe to use it again. Therefore, the syringe needs to be destroyed after used for safety's sake.

The present invention has arisen to mitigate or obviate the inconvenience and potential dangers of the conventional syringe.

SUMMARY OF THE INVENTION

The main objective of the present invention is to provide a breakable syringe with a safety sleeve, which can be broken immediately after use.

The other main objective of the present invention is to provide a breakable syringe with a safety sleeve that conveniently encloses a needle of the syringe to avoid from being stuck by the needle.

Further benefits and advantages of the present invention will become apparent after a careful reading of the detailed description with appropriate reference to the accompanying drawings.

DETAILED DESCRIPTION OF THE PREFERRED EMBODIMENT

A breakable syringe with a safety sleeve in accordance with the present invention comprises a syringe body with an optional piston shaft, a needle with an optional needle base, a safety sleeve, and a breaking device. The needle is attached to the syringe body by inserting the needle base into the syringe body. The safety sleeve movably sleeves the syringe body and clamps the breaking device with the syringe body. By sliding the safety sleeve, the safety sleeve can be selectively positioned at different locations to expose or enclose the needle by means of multiple engaging devices and even to urge the breaking device to break the syringe body. Therefore, the needle of the syringe is conveniently enclosed and the syringe can be immediately broken after use.

Figure 1:
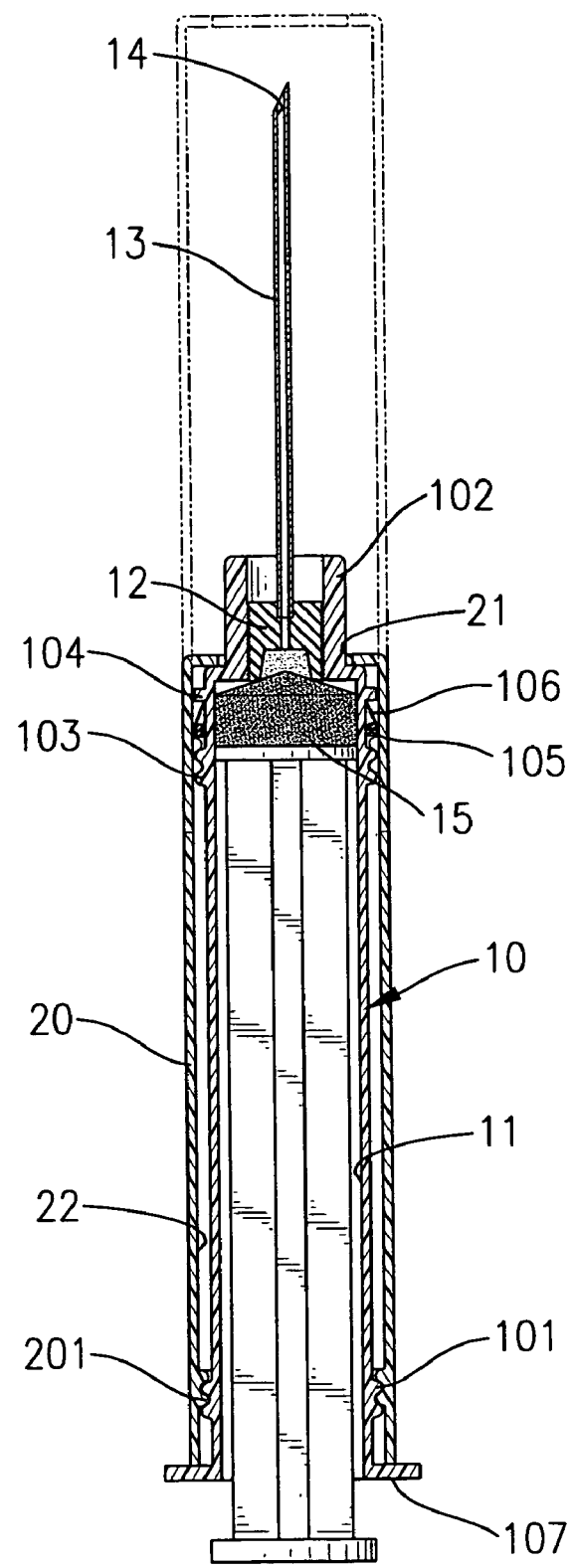
FIG. 1 is a side plane view of a breakable syringe with a safety sleeve in accordance with the present invention, wherein the broken lines show that the safety sleeve encloses a needle when the breakable syringe is not being used.
Figure 2:
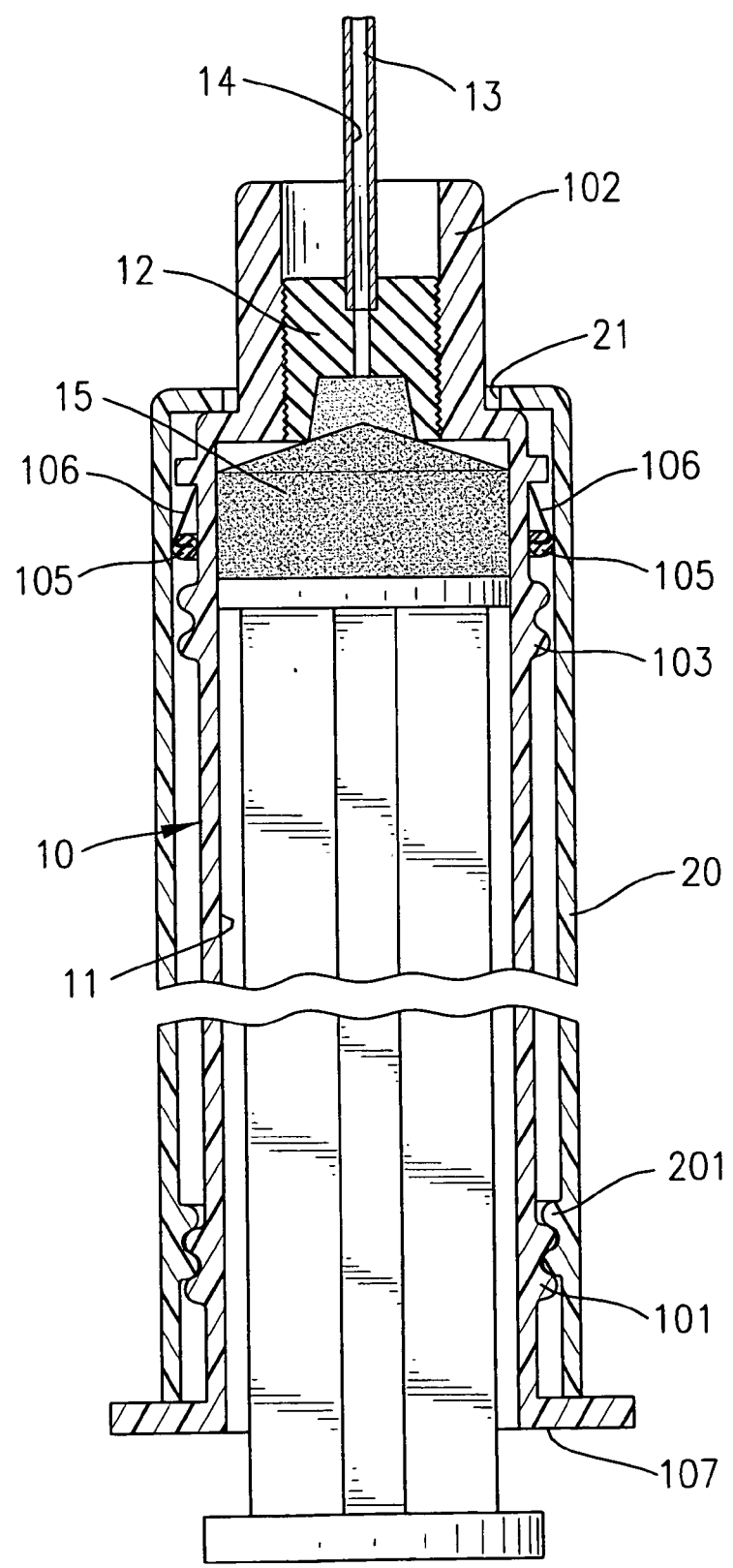
FIG. 2 is a partially enlarged side plane view of the breakable syringe with a safety sleeve in FIG. 1, wherein the needle is exposed.
Figure 3:
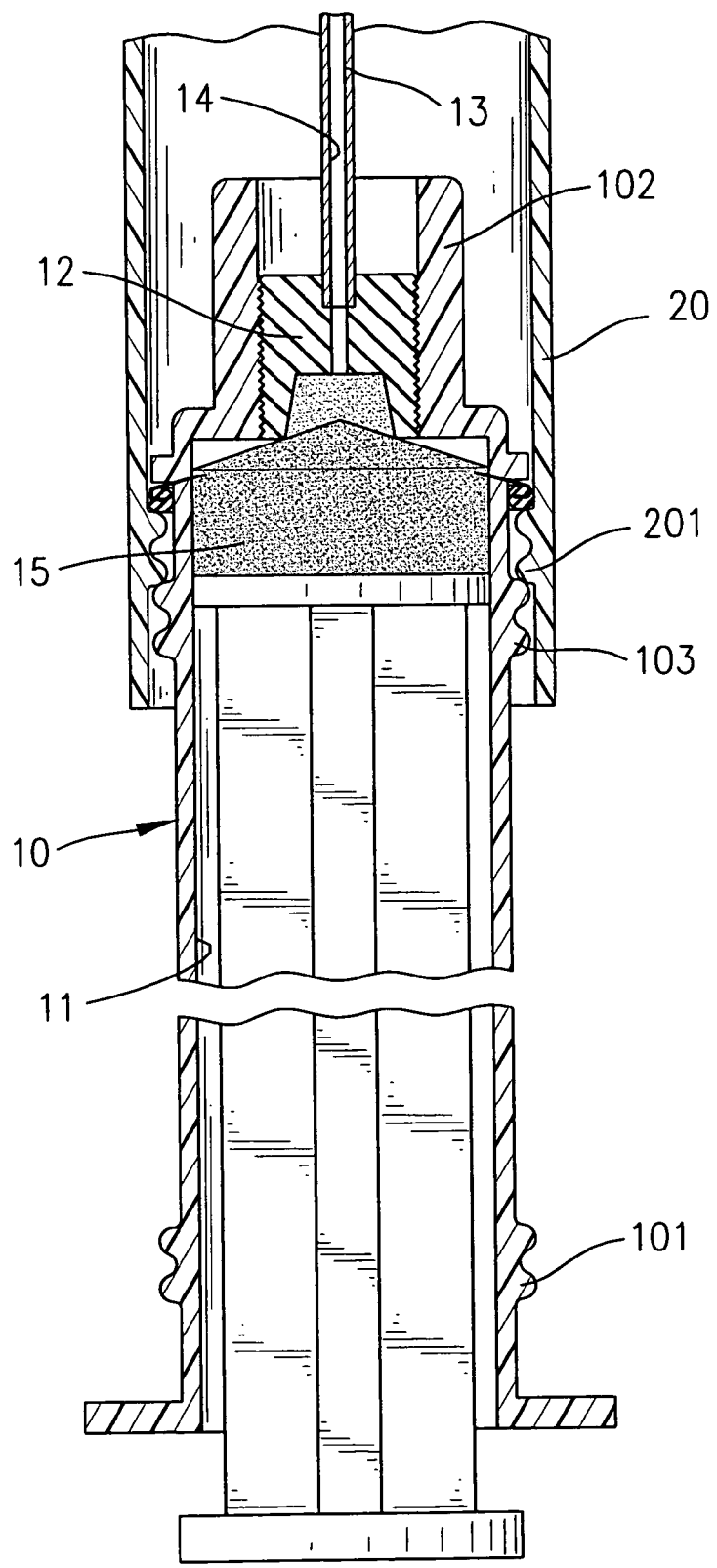
FIG. 3 is a partially enlarged side plane view of the breakable syringe with a safety sleeve in FIG. 1, wherein the needle is enclosed.

With reference to FIGS. 1 to 3, a first preferred embodiment of the breakable syringe with a safety sleeve in accordance with the present invention comprises a syringe body (10) with an optional piston shaft (15), a needle (13) with an optional needle base (12), a safety sleeve (20), multiple optional engaging devices and a breaking device.

The syringe body (10) is a cylindrical tube and has an inner chamber (11), an outer periphery, an open end with an outer rim (107), and a connecting end with a bore (102). The optional piston shaft (15) inserts into the inner chamber (11) via the open end and is slidably accommodated for pulling and pushing. The needle base (12) is inserted into the bore (102) and the needle (13) is partially received inside the needle base (12). Additionally, a passage (14) is defined through the needle (13) and the needle base (12) to communicate with the inner chamber (11) of the syringe body (10).

The safety sleeve (20) slidably sleeves the syringe body (10) and has an inner periphery, an abutting end, a distal end and an opening (21) defined in the distal end. Preferably, the safety sleeve (20) has a length the sameas the syringe body (10) and longer than the needle (13). When the safety sleeve (20) is completely pulled inward, the abutting end touches the outer rim (107) at the open end of the syringe body (10) and the distal end abuts on shoulders beside the bore (102) of the connecting end of the syringe body (10).

Figure 4:
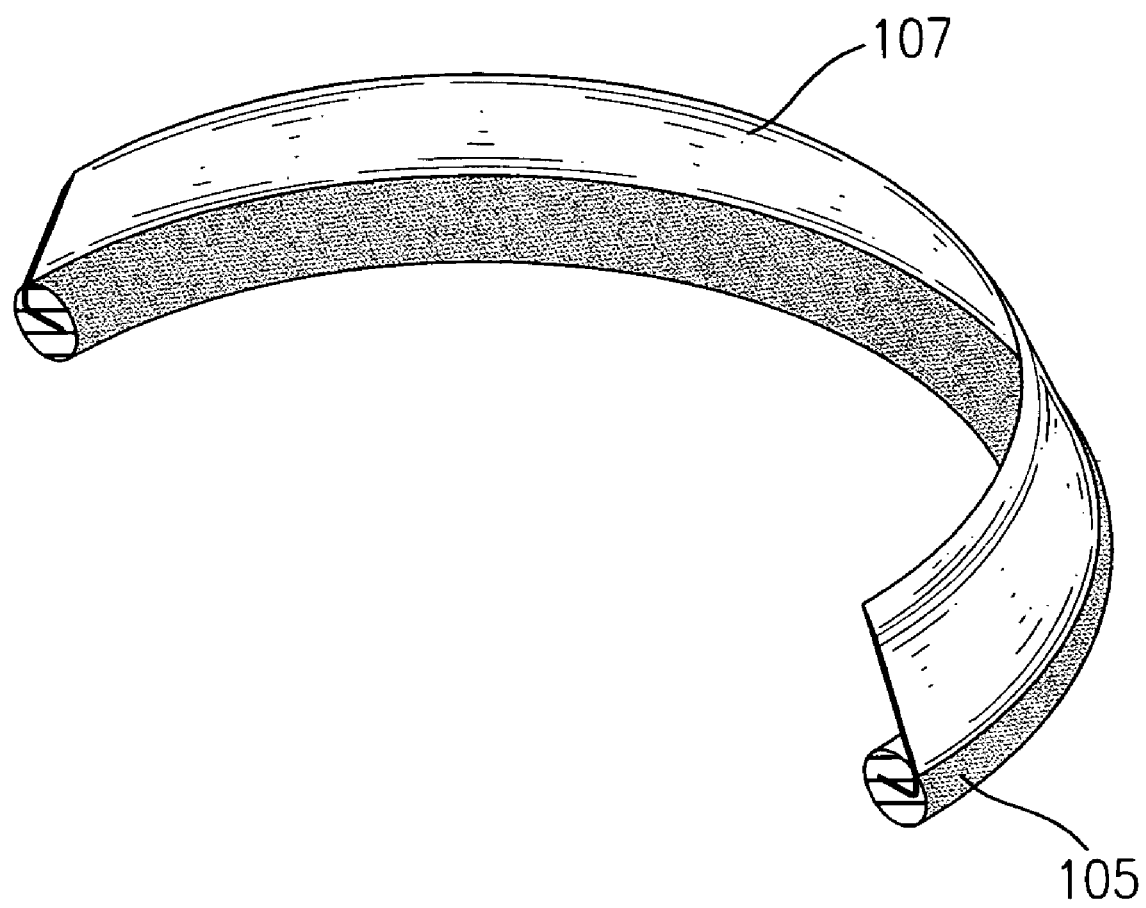
FIG. 4 is a perspective view of another embodiment of a breaking element.

The breaking device is clamped between the syringe body (10) and the safety sleeve (20) near the connecting end of the syringe body (10) and comprises a stop flange (104) and a breaking element. The stop flange (104) is formed on the outer periphery near the connecting end of the syringe body (10). The breaking element is movably located under the stop flange (104) and has a ring (105) surrounding the syringe body (10) and multiple pins (106) tapered to extend toward the syringe body (10) from the ring (105). Selectively, an annular blade (107) as shown in FIG. 4 can replace the pins (106) to mount on the ring (105).

The multiple engaging devices are multiple annular ribs respectively formed on the outer periphery of the syringe body (10) and the inner periphery of the safety sleeve (20). As shown in the figures, a pair of first annular ribs (101) is formed on the outer periphery near the open end of the syringe body (10). A pair of second annular ribs (103) is formed on the outer periphery near the connecting end of the syringe body (10) below the breaking device. Thereby, the breaking element is arranged between the stop flange (104) and the second annular ribs (103). Correspondingly, a pair of locking ribs (201) is formed on the inner periphery of the safety sleeve (20) to slidably and detachably engage with the first and second annular ribs (101, 103). Preferably, each of the multiple annular ribs (101,103) has a smooth surface to allow the annular rib (101,103) to slide pass the opposite locking ribs (201). Additionally, each of the locking ribs (201) also has a smooth surface.

When the locking ribs (201) engage with the second annular ribs (103), the safety sleeve (20) is mounted on the syringe body (10) to enclose the needle (13). When the syringe is to be used, the safety sleeve (20) is pulled inward to disengage the locking ribs (201) from the second annular ribs (103) so that the safety sleeve (20) moves toward the open end of the syringe body (10) to allow the needle (13) to emerge from the safety sleeve (20) via the opening (21). After the syringe has been used, the safety sleeve (20) is pulled outward and toward the open end of the syringe body (10) until the safety sleeve (20) crosses over the second annular ribs (103). Then, the locking ribs (201) push the ring (105) forward to urge the pin (106) to penetrate the syringe body (10) so that the syringe is not workable anymore.

Figure 5:
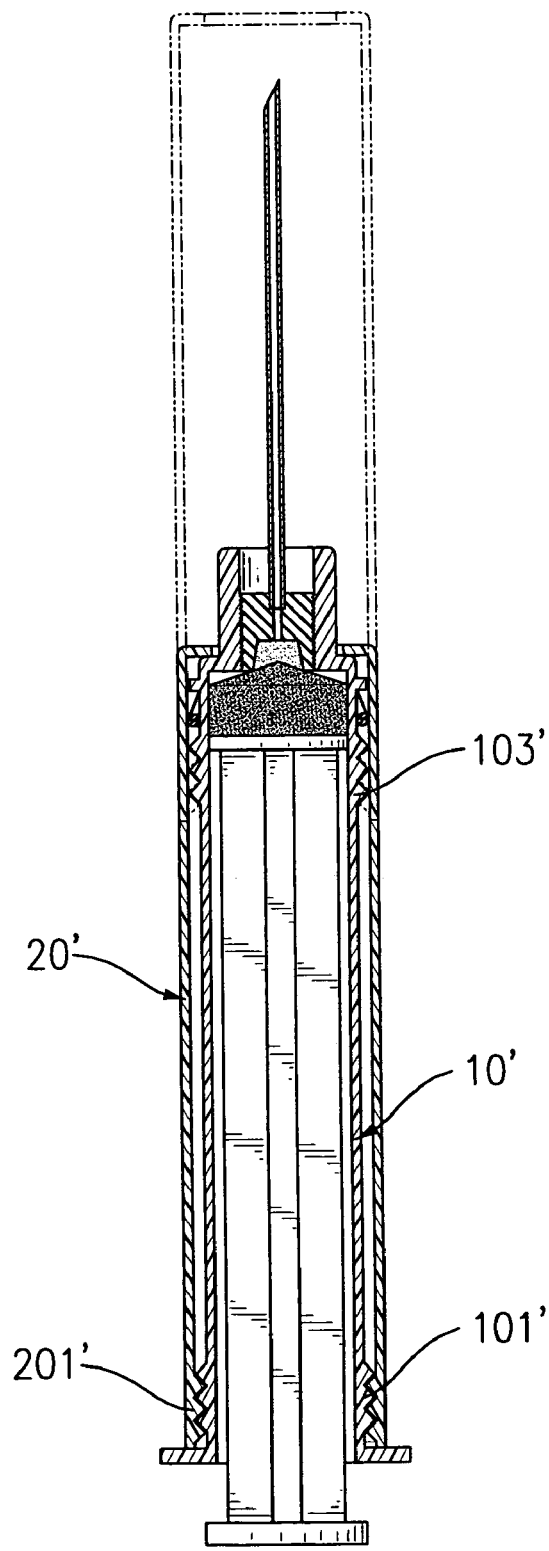
FIG. 5 is a side plane view of another embodiment of the breakable syringe with a safety sleeve in accordance with the present invention, wherein the safety sleeve is engaged by means of threads.

With reference to FIG. 5, a second embodiment of the breakable syringe with a safety sleeve in accordance with the present invention has the same structure with the first embodiment except the engaging devices. Multiple threads (101', 103',201') replace the multiple annular ribs. Therefore, the safety sleeve (20') is disengaged or engaged with the syringe body (10') by rotating the safety sleeve (20') relative to thesyringe body (10').

Figure 6:
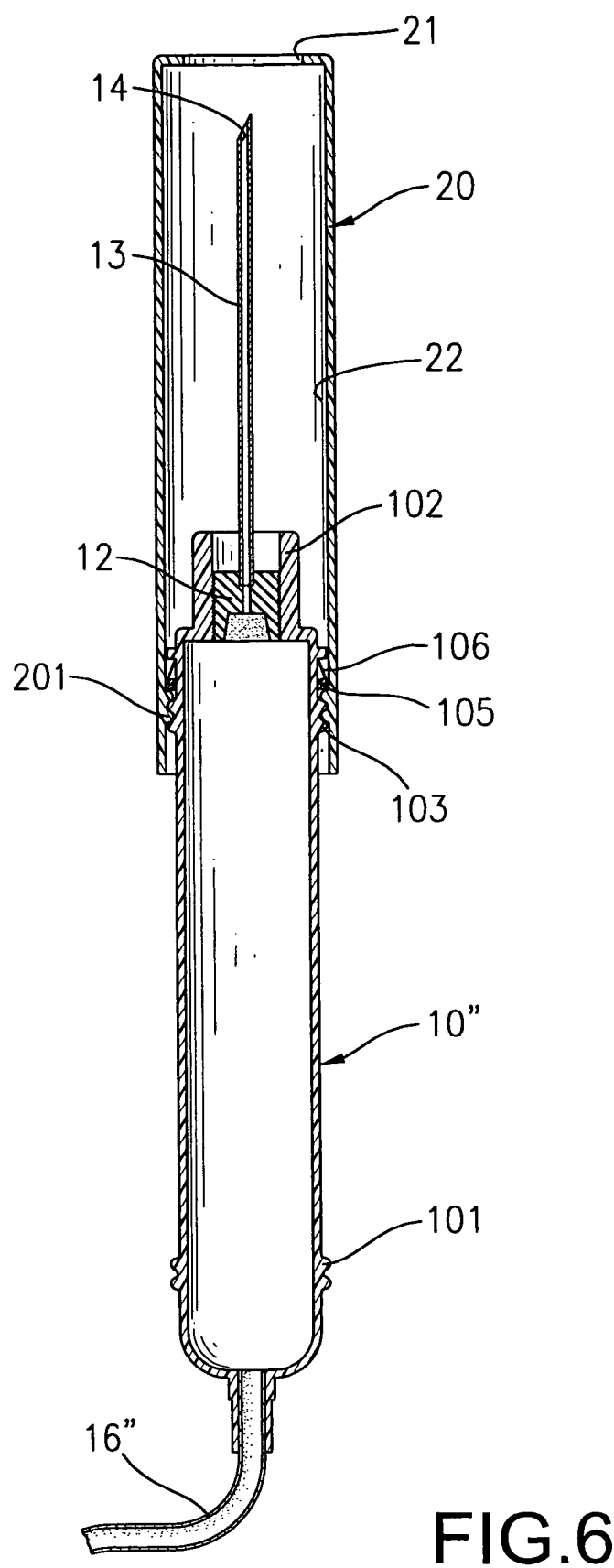
FIG. 6 is a side plane view of still another embodiment of the breakable syringe with a safety sleeve in accordance with the present invention, wherein the tube body is replaced by an automatic injecting tube.
Figure 7:
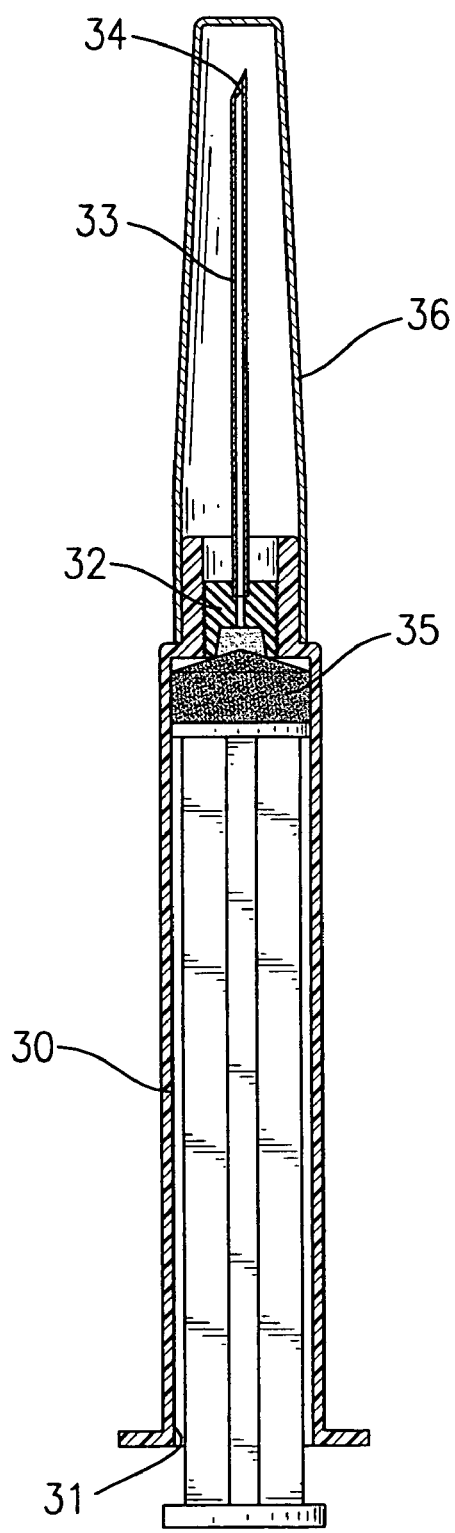
FIG. 7 is a side plane view of a conventional syringe in accordance with the prior art.

With reference to FIG. 6, a third embodiment of the breakable syringe with a safety sleeve in accordance with the present invention has the same structure with the first embodiment except for an automatically injecting tube (16") that replaces the piston shaft to integrally form at the open end of the syringe body (10").

According to the above description, the breakable syringe with a safety sleeve of the present invention has the following advantages:

1. The safety sleeve (20) can be conveniently moved to expose or to enclose the needle (13) on the breakable syringe by pushing the safety sleeve (20) to slide along the syringe body (10). Therefore, the safety sleeve (20) always aligns with the needle (13) to keep the safety sleeve (20) steady to receive the needle (13). The user is free from inadvertently touching the used needle (13) otherwise caused by mis-aligning the conventional cap.
2. The syringe body (10) can be broken by conveniently pushing the safety sleeve (20) to cross over the second annular ribs (103) to urge the pin (106) to penetrate the syringe body (10) after the syringe has been used.

Therefore, the syringe body (10) can not be used anymore and community hygiene requirements are thus met.

Although the invention has been explained in relation to multiple preferred embodiments, many other possible modifications and variations can be made without departing from the spirit and scope of the invention as hereinafter claimed.

What is claimed is:

1. A breakable syringe with a safety sleeve comprising:
    a syringe body being a cylindrical tube with an inner chamber an outer periphery, an open end, and a connecting end having
        a needle base inserted into the connecting end of the syringe body; and
        a needle partially received inside the needle base and having a passage defined through the needle and the needle base to communicate with the inner chamber of the syringe body;
    a safety sleeve slidably sleeving the syringe body, and being a tube with an inner periphery, an abutting end, a distal end and having a length longer than a length of the needle;
    a breaking device clamped between the syringe body and the safety sleeve near the connecting end of the syringe body to penetrate the syringe body by pushing with the safety sleeve; and
    multiple engaging devices respectively formed on the outer periphery of the syringe body and the inner periphery of the safety sleeve to locate the safety sleeve at multiple positions.

2. The breakable syringe with a safety sleeve as claimed in claim 1, wherein the multiple engaging devices comprising:
    a pair of first annular ribs formed on the outer periphery near the open end of the syringe body;
    a pair of second annular ribs formed on the outer periphery near the connecting end of the syringe body below the breaking device; and
    a pair of locking ribs formed on the inner periphery of the safety sleeve to detachably engage with the first and second annular ribs on the syringe body.

3. The breakable syringe with a safety sleeve as claimed in claim 2, wherein
    each of the locking ribs has a smooth surface; and
    each of the multiple annular ribs has a smooth surface to allow the annular rib sliding pass the locking ribs.

4. The breakable syringe with a safety sleeve as claimed in claim 1, wherein the breaking device comprises
    a stop flange formed on the outer periphery near the connecting end of the syringe body;
    a ring surrounding the syringe body; and
    a pin abutting stop flange and tapered to extend toward the syringe body from the ring.

5. The breakable syringe with a safety sleeve as claimed in claim 3, wherein the breaking device comprises
    a stop flange formed on the outer periphery near the connecting end of the syringe body;
    a ring surrounding the syringe body; and
    multiple pins abutting stop flange and tapered to extend toward the syringe body from the ring.

6. The breakable syringe with a safety sleeve as claimed in claim 1, wherein the breaking device comprises:
    a stop flange formed on the outer periphery near the connecting end of the syringe body;
    a ring surrounding the syringe body; and
    an annular blade abutting stop flange and tapered to extend toward the syringe body from the ring.

7. The breakable syringe with a safety sleeve as claimed in claim 1, wherein the multiple engaging devices comprising:
   multiple threads respectively formed on the outer periphery of the syringe body and the inner periphery of the safety sleeve.

8. The breakable syringe with a safety sleeve as claimed in claim 4, wherein the multiple engaging devices comprising:
   multiple threads respectively formed on the outer periphery of the syringe body and the inner periphery of the safety sleeve.

9. The breakable syringe with a safety sleeve as claimed in claim 5, wherein the breakable syringe further has a piston shaft accommodated inside the chamber.

10. The breakable syringe with a safety sleeve as claimed in claim 8, wherein the breakable syringe further has a piston shaft accommodated inside the chamber.

11. The breakable syringe with a safety sleeve as claimed in claim 5, wherein the breakable syringe further has an automatically injecting pipe connected with the open end of the syringe body.

12. The breakable syringe with a safety sleeve as claimed in claim 8, wherein the breakable syringe further has an automatically injecting pipe connected with the open end of the syringe body.

* * * * *